(12) United States Patent
Göbel

(10) Patent No.: US 12,257,408 B2
(45) Date of Patent: Mar. 25, 2025

(54) DEVICE FOR TAMPONADE SEALING PROTECTION OF SURGICAL SUTURES AND WOUNDS, IN PARTICULAR OF END-TO-END ANASTOMOSES OF THE RECTUM

(71) Applicant: Advanced Medical Balloons GmbH, Waghäusel (DE)

(72) Inventor: Fred Göbel, Lützelbach (DE)

(73) Assignee: Advanced Medical Balloons GmbH (DE)

( * ) Notice: Subject to any disclaimer, the term of this patent is extended or adjusted under 35 U.S.C. 154(b) by 748 days.

(21) Appl. No.: 17/424,411

(22) PCT Filed: Jan. 24, 2020

(86) PCT No.: PCT/IB2020/050563
§ 371 (c)(1),
(2) Date: Jul. 20, 2021

(87) PCT Pub. No.: WO2020/152640
PCT Pub. Date: Jul. 30, 2020

(65) Prior Publication Data
US 2022/0105320 A1    Apr. 7, 2022

(30) Foreign Application Priority Data

Jan. 24, 2019  (DE) .................... 10 2019 000 474.4

(51) Int. Cl.
*A61M 25/10*  (2013.01)
*A61B 17/11*  (2006.01)
*A61M 27/00*  (2006.01)

(52) U.S. Cl.
CPC .... *A61M 25/10184* (2013.11); *A61B 17/1114* (2013.01); *A61M 25/1002* (2013.01);
(Continued)

(58) Field of Classification Search
CPC .............. A61M 25/10; A61M 25/1002; A61M 25/1011; A61M 25/1018;
(Continued)

(56) References Cited

U.S. PATENT DOCUMENTS

2005/0033226 A1* 2/2005 Kim ..................... A61F 2/04
604/101.01
2005/0054996 A1* 3/2005 Gregory ................ A61F 5/442
604/317
(Continued)

FOREIGN PATENT DOCUMENTS

CN   202590135   12/2012
DE   102012003034   8/2012
(Continued)

*Primary Examiner* — Robert A Lynch
(74) *Attorney, Agent, or Firm* — Pandiscio & Pandiscio

(57) ABSTRACT

The invention is directed to a device (1) for sealingly protective and at the same time stool-discharging tamponade of a circular anastomosis of two ends of the large intestine, as occur for example in the surgical resection of a rectal carcinoma, wherein a thin-walled balloon body (5) is placed in the region of the anastomosis, and the balloon (5), providing a tamponade, is filled with a filling medium in such a way that the lowest possible pressure necessary for the sealing tamponade of the anastomosed portion of the intestine can be maintained continuously, and, even in the event of a peristaltic contraction of the rectosigmoid colon, the pressure predefined by the user is maintained as constant as possible, wherein sufficiently high volumetric flows of the pressurizing medium supplied to and removed from the balloon (5) are achieved, such that the sealing contact between the balloon (5) and the intestinal wall is maintained in all segments of the balloon body in the course of a peristaltic contraction wave miming from the sigmoid to the anus.

60 Claims, 9 Drawing Sheets

(52) U.S. Cl.
CPC ...... *A61M 27/00* (2013.01); *A61B 2017/1132* (2013.01); *A61M 2025/1004* (2013.01); *A61M 2025/1059* (2013.01); *A61M 2025/1072* (2013.01); *A61M 2210/1064* (2013.01); *A61M 2210/1067* (2013.01)

(58) Field of Classification Search
CPC .... A61M 25/10184; A61M 2025/1004; A61M 2025/1059; A61M 2025/1072; A61M 27/00; A61M 2210/1064; A61M 2210/1067; A61B 17/11; A61B 17/1114; A61B 2017/1132
See application file for complete search history.

(56) References Cited

U.S. PATENT DOCUMENTS

| | | | | |
|---|---|---|---|---|
| 2009/0143722 A1* | 6/2009 | Kim | ...................... | A61M 3/022 604/28 |
| 2014/0358126 A1* | 12/2014 | Gobel | ................. | A61M 3/0295 604/328 |
| 2017/0173310 A1* | 6/2017 | Gregory | .......... | A61M 25/10187 |
| 2018/0333552 A1 | 11/2018 | Göbel | | |

FOREIGN PATENT DOCUMENTS

| | | |
|---|---|---|
| DE | 102015002995 | 9/2016 |
| EP | 1492585 | 1/2005 |
| WO | WO 2013/026564 | 2/2013 |

\* cited by examiner

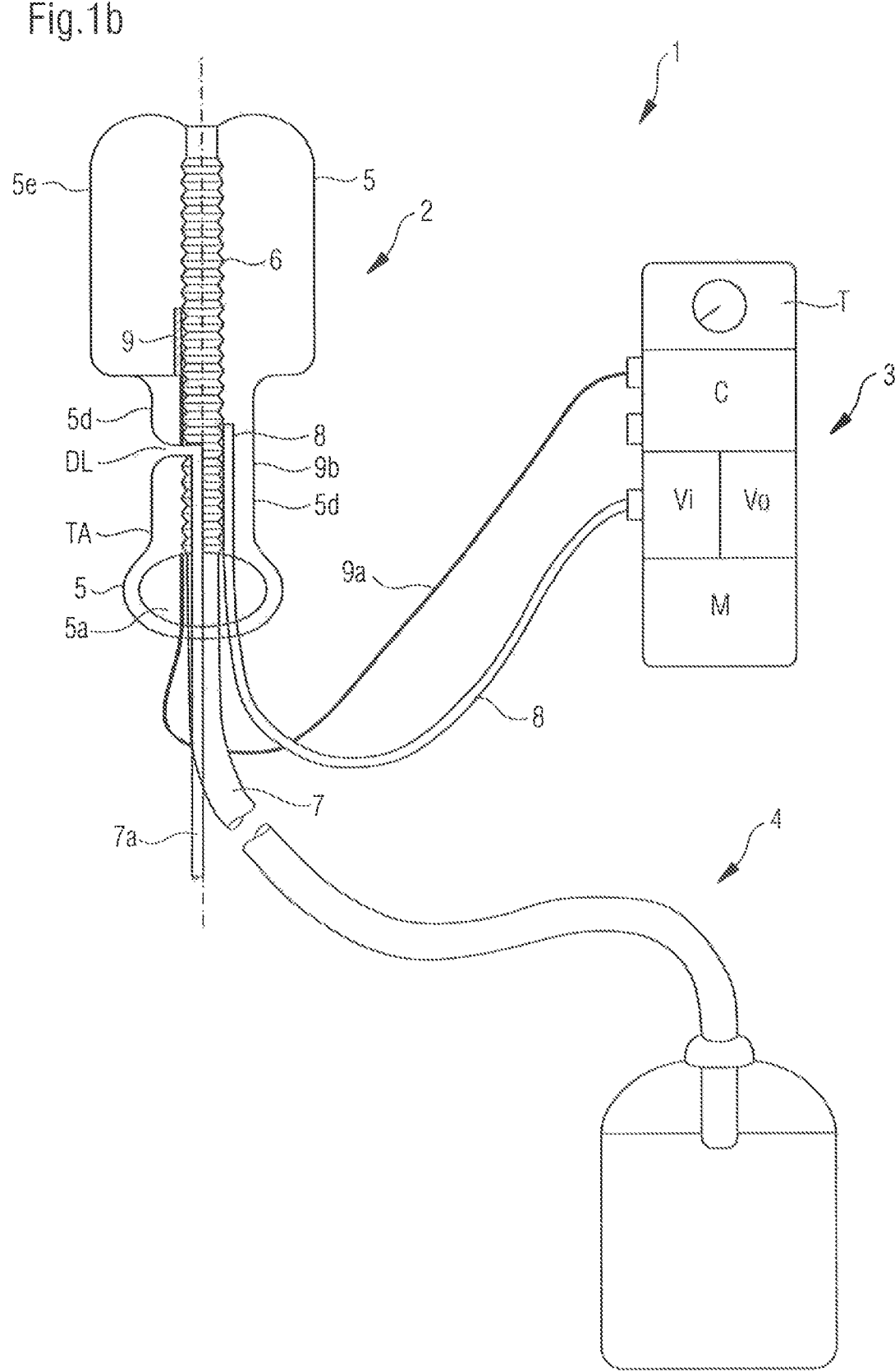

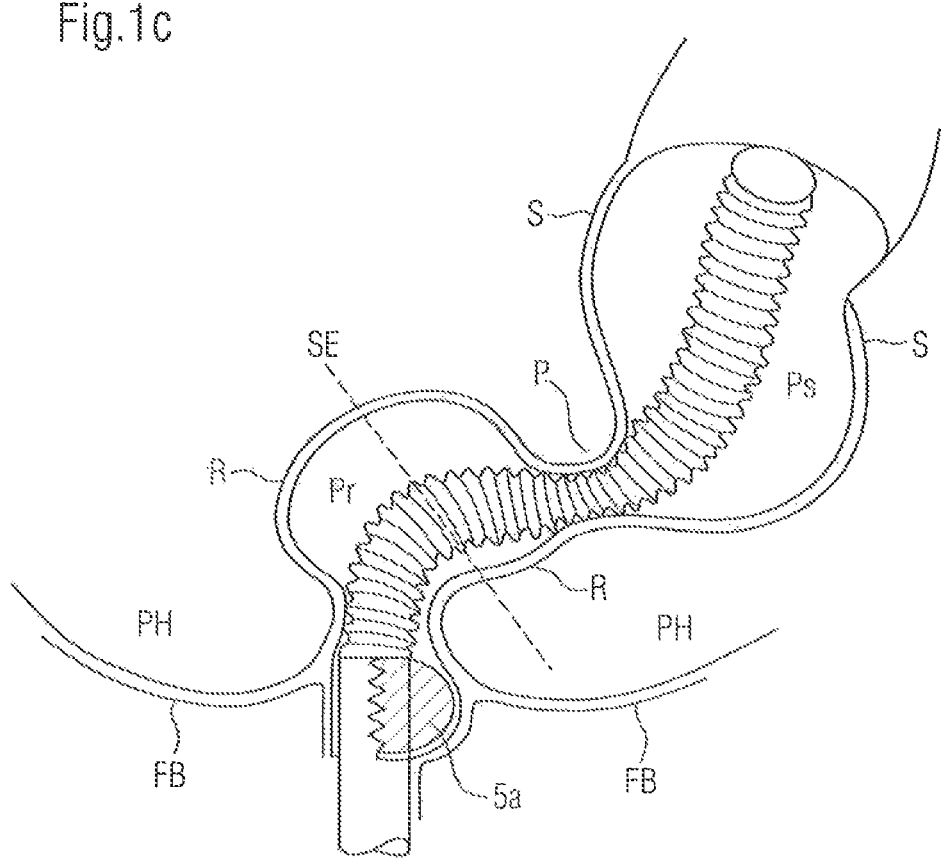

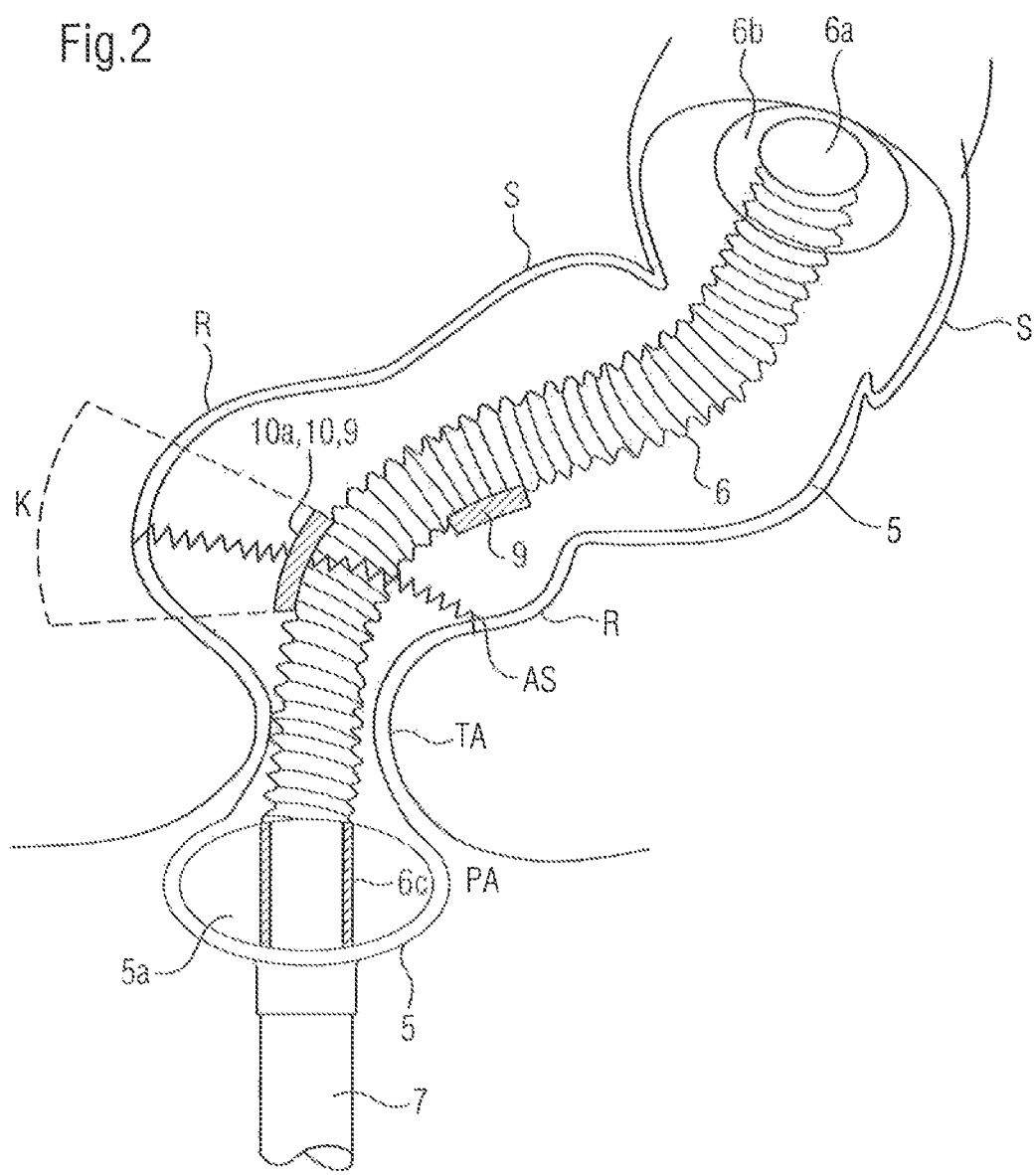

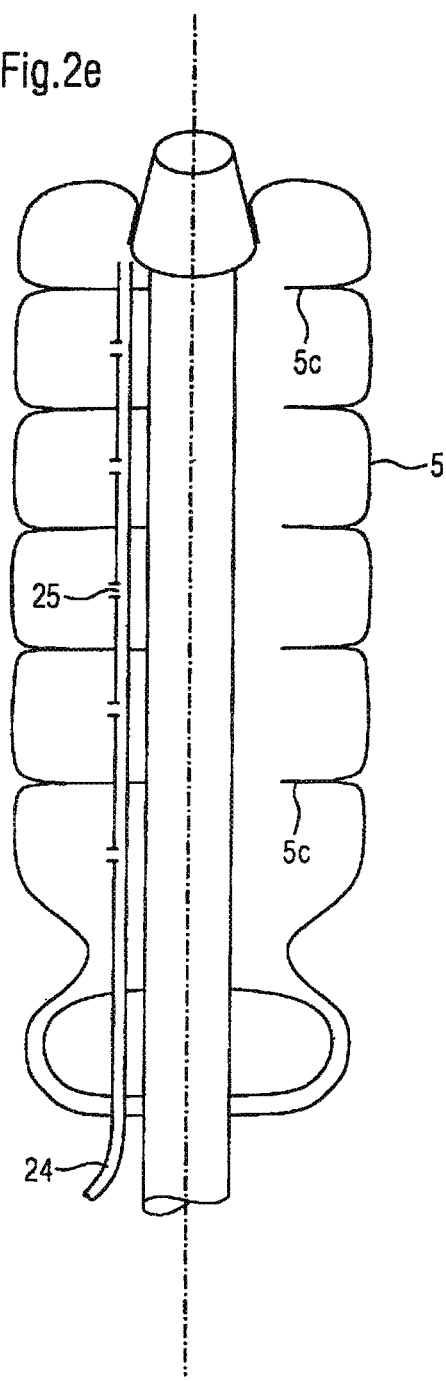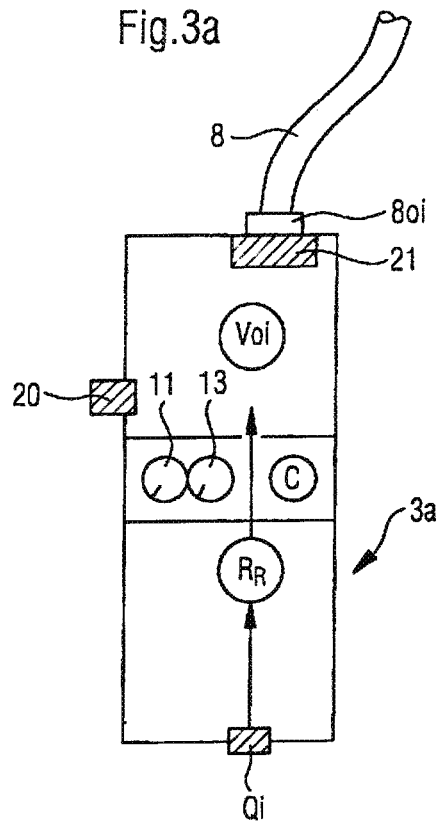

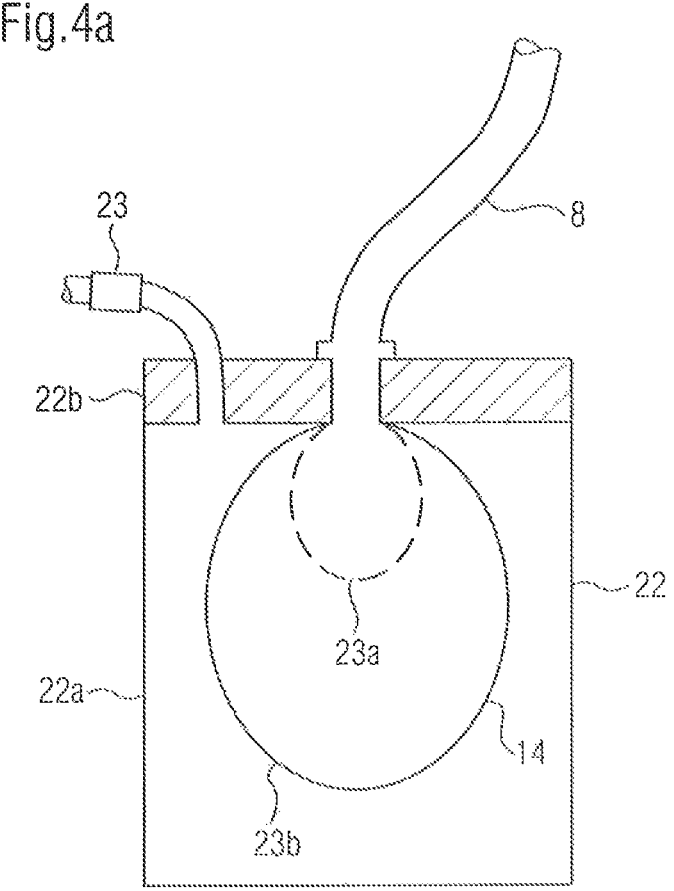

DEVICE FOR TAMPONADE SEALING PROTECTION OF SURGICAL SUTURES AND WOUNDS, IN PARTICULAR OF END-TO-END ANASTOMOSES OF THE RECTUM

REFERENCE TO PENDING PRIOR PATENT APPLICATIONS

This patent application claims benefit of International (PCT) Patent Application No. PCT/IB2020/050563, filed 24 Jan. 2020 by Creative Balloons GmbH for DEVICE FOR TAMPONADE SEALING PROTECTION OF SURGICAL SUTURES AND WOUNDS, IN PARTICULAR OF END-TO-END ANASTOMOSES OF THE RECTUM, which claims benefit of German Patent Application No. DE 10 2019 000 474.4, filed 24 Jan. 2019.

The two (2) above-identified patent applications are hereby incorporated herein by reference.

FIELD OF THE INVENTION

The invention is directed to a device and a method for the sealing protection, with tamponading action, of a surgically applied circular anastomosis between an oral end and an aboral end of the large intestine, in particular the rectum or sigma, or some other suture or lesion present in this portion of the intestine, at the same time with a stool-discharging function through the segment of the intestine that is anastomosed, injured, or treated surgically or via some other intervention, and with subsequent passage of the stool through the anal sphincter.

BACKGROUND OF THE INVENTION

In the resection of tumors in the region of the rectum and the sigmoid colon, round sutures that make an "end-to-end" connection of the oral and aboral ends of the intestine, severed during the resection, are generally applied. In the majority of cases, the anastomosis takes place using annularly arranged metal clips that connect the two ends of the intestine and restore the continuous lumen of the intestine. The clipping is carried out using specialized applicators, so-called staplers, that are inserted through the anus of the patient and into the region of the intestine to be connected. It is known that in approximately 10 percent of all end-to-end anastomoses carried out in this way, so-called suture insufficiency, which is generally caused by reduced vascular perfusion in the clipped region, results. In the worst case this leads to necrotic ischemia of the intestinal wall near the anastomosis and the escape of intestinal contents into the abdominal area, which generally results in serious, life-threatening inflammatory complications. For resections of segments of the large intestine, in particular in the region of the deep rectum, so-called relieving ileostomies are therefore carried out as a preventive measure. The intestinal contents are discharged through the abdominal wall far above the rectum, generally in the region of the small intestine, into a collection bag via a surgically applied artificial anus, a so-called stoma. The advancement of stool into the intestine, which is anastomosed with the coronal suture, is thus prevented, and an accumulation of stool which places stress on the anastomosis or possible dilation of the joined ends of the intestine is avoided. After the anastomosis heals, the stoma is relocated, and elimination once again takes place in the normal manner. The surgical application and relocation of a stoma as well as the course of a stoma therapy itself are not free of complications, and in many cases require surgical revision.

For the care of patients undergoing rectal resection, an alternative technique would therefore be desirable, so that the application of a protective stoma may in principle be dispensed with.

By continuously modifying the stools of the patient in the thin liquid range, it is currently possible to discharge stool via catheter-like stool drains permanently situated in the rectum of a patient. These so-called "indwelling drainage" systems generally have an intrarectally anchored balloon with an approximately toroidal shape, placed on the end of a stool-discharging tube. These first-generation systems having a simple design are predominantly made of silicone. For several years, systems made of polyurethane and having a more complicated construction have supplemented the prior art. In these PUR-based designs the balloon body is dumbbell-shaped, the middle portion with a tapered diameter being positioned in the anal canal or extending through the anal canal. The dumbbell-shaped balloon rests in a shaft tube that is elastically deformable in the anal canal. Thus, in the transanal segment of the PUR-based device, the shaft tube and the tapered balloon portion are situated concentrically with respect to one another, thus allowing sealing of the anal canal that is synchronous with the anal sphincter. The inner tube layer discharges the stool through the anus, while the transanal balloon segment lies closely against the anal mucosa in a continuously sealing function, spontaneously and adaptively following the particular position of the anal sphincter. The force required for the adaptive transanal sealing is absorbed by the rectal segment of the dumbbell-shaped balloon body. The new systems are filled with a defined, specified balloon volume, conceptually resulting in a slack, unstretched state of the balloon. The pressure prevailing in each case in the transanally positioned balloon results, in conjunction with the instantaneous rectal motility or the instantaneously acting rectal forces. A corresponding device having this design for continuous stool discharge is described in PCT/EP2012/003534. However, this is a largely passive arrangement; although the pressure within the balloon is reduced in relation to silicone-based balloons, for the application for a freshly performed resection, for a sufficiently sealing placement of such a balloon inside the colon it would still be necessary, due to peristaltic movements in the colon, to select a pressure that is routinely set too high, resulting in damage to the highly sensitive tissue after the resection procedure.

SUMMARY OF THE INVENTION

These disadvantages of the described prior art have resulted in the object initiating the invention, to find an option that allows the application of a protective stoma to be basically dispensed with, without damaging the tissue recently subjected to surgery in the region of the anastomosis.

This object is achieved using at least one thin-walled balloon body, formed completely to its working dimensions during manufacture and made of a material with preferably low volume expandability, for placement in the region of the anastomosis in such a way that its distal balloon end or its distal balloon segment, orally with respect to the anastomosis, extends in the region of the rectum or sigma of the patient or also beyond the sigma, the balloon body enclosing a flexibly and/or elastically deforming tube element that passes through the balloon body from its distal or oral end or balloon segment to its proximal or aboral end or balloon segment, where it is connected or connectable to an extracorporeal tube, the tamponading balloon body being connected via a tubular feed and discharge line to an extracorporeal apparatus which actively controls or passively allows the supply and discharge of a filling medium to and from the balloon body in such a way that in the tamponading balloon body, the lowest possible filling pressure necessary for the sealing tamponade of the anastomosed portion of the intestine but also a pressure that is sufficient in order to not damage tissue in the region of the anastomosis, and that continuously compensates for mass movements of the abdomen and in particular peristaltic contractions of the intestine, is maintained, so that the tamponading sealing contact of the balloon body with respect to the intestinal wall remains consistent without damaging the intestinal wall in the region of the anastomosis.

The distal or oral end of the balloon body should be situated orally with respect to the anastomosis so that it remains protected from stool via the sealing closure of the colon upstream from the anastomosis, whereas the position of the proximal or aboral end of the balloon body is not limited to a certain location. In the case of a greatly shortened balloon body, the proximal end thereof may also be situated orally with respect to the anastomosis. In such a case, the interior shaft tube would extend largely exposed within the colon.

In such an arrangement, maintaining the predefined position of the balloon body is also transferred to the shaft tube. The shaft tube should then have sufficient structural stability to allow a position, determined starting from the anus, to be passed on to the balloon body situated in the rectum or sigma. At the same time, the shaft tube should also have sufficient flexibility to be able to follow the windings of the colon.

On the other hand, to allow contact between the shaft tube and the anastomosis to be reliably excluded, the invention recommends placing the proximal balloon end at least aborally with respect to the anastomosis, or to extend it to the anus or even provide it preanally.

Thus, the invention [provides] a drain-like device, having a tamponading action for discharging liquid stools, that is transanally inserted into the freshly resected and anastomosed rectum of the patient, and that receives liquid modified stool 5 to 15 cm, preferably 10 cm, above the anastomosis, depending on the particular postoperative site, and discharges it normally through the anus, past the anastomosis suture, and into a stool-collecting container outside the body. The device is made up essentially of a stool-receiving and stool-discharging tube film or film-like tube component that adapts to and follows the anatomical axial course of the intestine, and spontaneously elastically straightens out to its particular profile formed during manufacture. The elastically deforming and straightening film tube bears a membrane-like, thin-walled balloon body that is cylindrical or also provided with haustra-like circular constrictions, and that extends from the base of the rectum into the sigma of the patient or also beyond the sigma. The balloon body has already been formed to its complete working dimensions during manufacture. Its diameter corresponds to the diameter of the respective freely unfolded, completely atonal rectum and/or sigma. In the preferred case, the diameter of the balloon body exceeds the rectosigmoidal diameter to be assumed, and then has so-called residual dimensioning. In the preferred embodiment, the balloon also has a transanal segment that adjoins the rectal segment. The transanal segment is positioned inside the anal canal and carries the balloon body through the anal canal. The transanal balloon portion is preferably provided with a diameter that corresponds to or exceeds a fully open anus. Thus, an advantageous radial folding-in of the residual envelope wall, in excess of the diameter, results when the anal sphincter is partially open. Upstream from the anus, the balloon body optionally expands once again into a spherical or discoid-shaped preanal segment. A separately fillable inner balloon having an anchoring action or an abutment element, with a corresponding anchoring action, having some other design may be installed inside the preanal balloon segment. As an alternative to a balloon-based fixing of the device in the region of the perianal skin, within the scope of the invention a flatly adhering fixing element that acts as an abutment may be used.

The dumbbell-shaped balloon body is filled by a particularly large-lumen, tube-like feed line from a volume reservoir or a machine controller outside the body. In the preferred embodiment of the invention, the filling takes place using a quick-controlling, high-flow valve system that is driven by an appropriately dimensioned pressure gradient and that actively conveys volume into the balloon and/or actively withdraws volume from the balloon. The particular prevailing filling pressure within a balloon that tamponades the intestinal lumen or closes off the intestinal cross section is preferably continuously detected by an electronic pressure sensor inside the tamponading or sealing balloon body. It is an essential feature of the device that peristaltic contractions of the sigma and of the rectum are compensated for by adapting the balloon filling volume, and thus during the course of the peristaltic contraction a tamponading or sealing setpoint filling pressure specified by the user may be maintained in the tamponading balloon, or transient, critically high filling pressures may be avoided. In addition, the peristalsis-related expulsion of the device from the rectosigmoid or dislocation from its transanal position, necessary for the suture-protective function, may be avoided by appropriate control of the filling volume in the balloon.

During a peristaltic contraction of the terminal portion of the colon, the volume- and pressure-controlling mechanism connected to the device ensures a constant setpoint pressure in the tamponading balloon, specified by the user, which is necessary for protecting the anastomosis. When the peristaltic contraction subsides, or when the tonus of the intestinal wall decreases, with a corresponding dilation of the intestinal lumen, the controlling mechanism supplies the balloon body with filling volume in a controlled manner in such a way that the setpoint pressure specified by the user, and thus the tamponading, protective effect of the balloon envelope on the anastomosed intestinal wall, is consistently maintained over the entire course of the contraction. The supplying and discharging of volume to and from the balloon preferably take place using electronically controlled proportional valves that control in a particularly rapid and precise manner.

As an alternative to the technically relatively complicated electronic control of the balloon volume and balloon filling pressure, a relatively simply constructed extracorporeal reservoir balloon that may be comfortably worn by the patient may be connected to the filling line for the device having a tamponading/draining action. The reservoir has a special balloon that is volume-expandable in a specific manner and made of isoprene-like material, for example, and that allows an essentially isobaric pressure profile over a certain expansion range of the balloon wall or the filling state of the balloon. Filling medium may thus be displaced in both directions between the balloon body of the catheter device and the controlling reservoir, without exceeding a maximum pressure in the overall system that is determined by the reservoir via mechanical expansion. This simple design of a controlling component is preferably used in the subsequent postoperative care phase, in which the suture area has already stabilized and particularly precise and rapid control is no longer the primary requirement.

Moreover, the invention discloses a method and a system for sealingly protective and at the same time stool-discharging or -conducting tamponade of a circular anastomosis of two ends of the large intestine, as occur for example in the surgical resection of a rectal carcinoma, wherein after placement of the anastomosis by the surgeon, using a circular suture or a circular staple clipping, a catheter-like device having a diameter that corresponds to or exceeds the diameter of the atonal colon is inserted into the postoperative site, the balloon during manufacture already having been formed to its dimensions necessary for the tamponade according to the invention, and the balloon body having a constriction-like taper in the transanal segment that is suitable for transanal positioning of the device, and preanally having a spherical enlargement that encloses a preanal retention element, and the portion of the balloon body extending into the colon filling at least the rectum of the patient, but optionally also the entire rectosigmoid. The balloon body is carried by a flexibly bendable shaft tube that follows the windings of the rectosigmoidal intestine with as little tension as possible, and that radially folds in and straightens in an elastic manner, in particular in the transanal segment. After the device is inserted in the proper transanal position by the surgeon, the balloon of the tamponading device is connected to an electronically regulated control unit that acts on the balloon with a setpoint pressure that is selected by the user, and consistently maintains this pressure to compensate for peristaltic contractions and mass movements of the abdomen due to rapid supplying or removal of filling medium. The setpoint pressure is typically in the range of 5 to 30 mbar, preferably 10 to 15 mbar.

BRIEF DESCRIPTION OF THE DRAWINGS

Further features, particulars, advantages, and effects based on the invention result from the following description of preferred embodiments of the invention and with reference to the drawings. In the drawings:

FIG. 1b shows one embodiment which in the region of the anastomosis has a special constricted region that lies fairly closely against the interior shaft tube;

FIG. 1c shows a special embodiment of the invention for the perianally adherent fixing of the catheter device;

FIG. 2 shows a special embodiment of the invention in situ, in the transanally positioned location;

FIG. 2e shows a special design of a tamponade balloon that is provided with circular constrictions;

FIG. 3a shows a simplified controller unit;

FIG. 4a shows a portable embodiment of an isobarically controlling reservoir corresponding to FIG. 4.

DETAILED DESCRIPTION OF THE PREFERRED EMBODIMENTS

Figure 1:
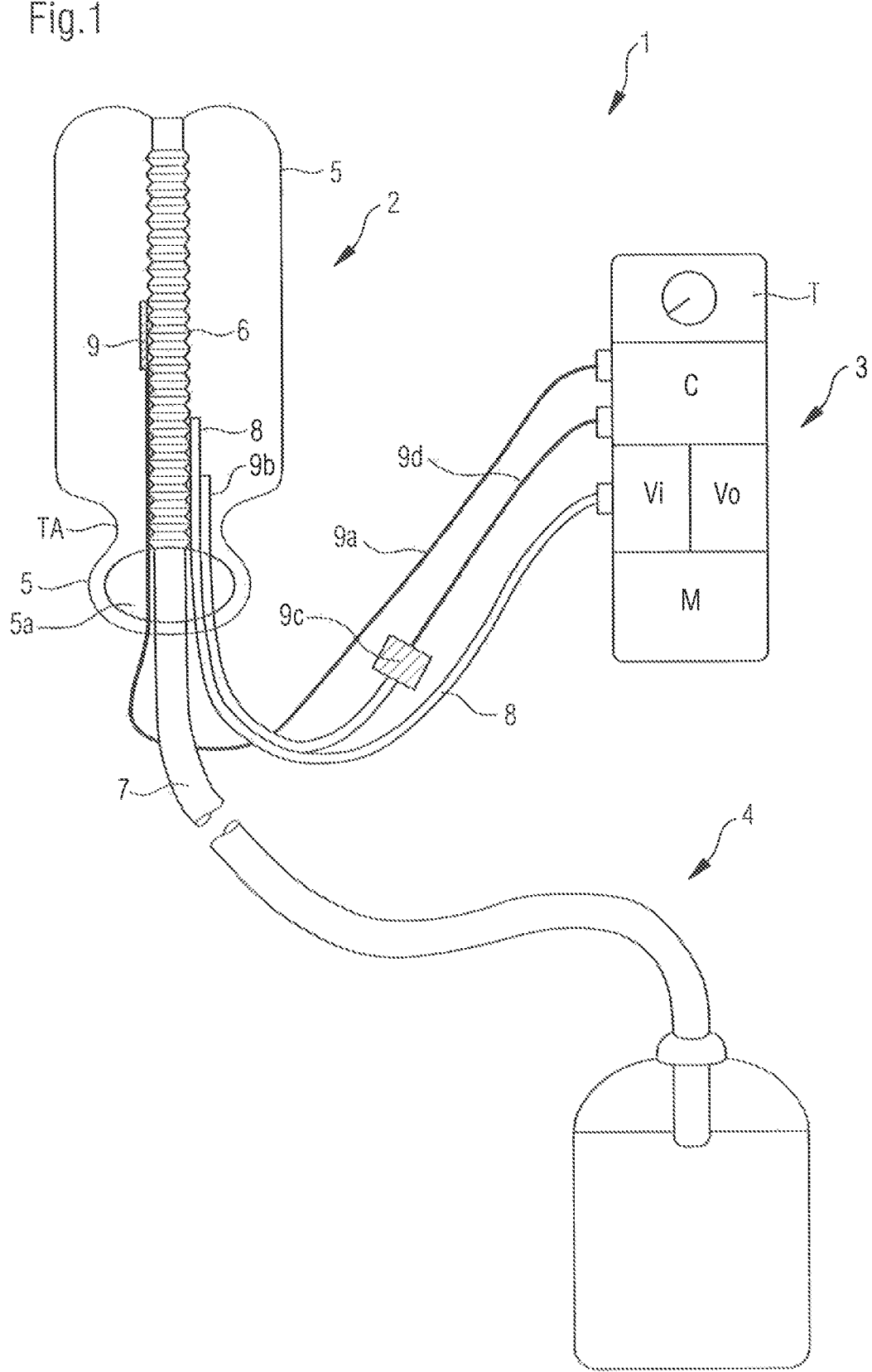
FIG. 1 shows a device according to the invention in a schematic overview, comprising an intracorporeal tamponading balloon catheter for the dynamic, controlled adaptation to changing volumes and pressures in the intestinal lumen, an extracorporeal controller unit that is connected to the balloon catheter, and a stool collection container.

FIG. 1 shows the device 1 for the protective tamponade of anastomosed portions of the intestine connected end-to-end, the anastomosis being produced by a lumen-preserving surgical suture or a surgical clipping or stapling of the intestinal segments to be connected, the device comprising the catheter portion 2, an extracorporeal controller unit 3, and a stool-discharging and stool-collecting container 4.

The catheter portion 2 remains in the body of the patient for the entire time the device is used. In the illustrated embodiment, the catheter portion is made up of a dumbbell-shaped balloon element 5 that rests on a flexibly bendable tube element 6 that closely follows the windings of the rectosigmoid colon, and which under corresponding action of force by the intestine, or also upon corresponding mass movements of the body or of the abdomen, elastically collapses, and when the force diminishes, elastically straightens back into its particular profile specified by the manufacture. In the directly preanal position, the tube element carries a retention element 5a, which in the preferred embodiment of the device is completely enclosed by the envelope of the balloon 5. In modified designs of the device, the retention element may also adjoin the proximal end of the balloon element 5, in which case the proximal end of the balloon body terminates with the external opening of the anus at approximately the same level. The retention element 5a may be a balloon-like body, but may also be made of gel-like or foam-like materials. The element ensures that the device remains in the position necessary for its protective and draining function and does not become dislocated from the transanal position and into the rectum. The transanal taper TA of the balloon element is placed in the patient via the anal sphincter or inside the anal canal. The elastically deformable tube element 6 in the extracorporeal direction merges into a discharging tube 7, which connects the head part of the device to the collector 4. The discharging tube is preferably made of a film tube-like material, and thus may collapse to form a flat, ribbon-like structure under stress or when the patient is lying down.

The filling of the balloon element 5 takes place via a large-lumen, flexibly bendable, lumen-stable feed line 8 whose diameter and length are dimensioned in such a way that the gas volumes necessary for the dynamic tamponade sought according to the invention may be discharged from the balloon and led into the balloon with sufficient speed, and not hindered by excessively high flow resistance. The feed line 8 inside the balloon-carrying portion of the device has an internal diameter of 4 to 8 mm, preferably 5 to 6 mm. In the proximal region of the feed line, i.e., in the preanal transition area to the extracorporeal portion of the device, the flow-effective diameter may be increased to 7 to 12 mm, preferably 7 to 8 mm. The feed line 8 may be stabilized, for example, by a coil that is integrated into the wall of the feed line to provide reinforcing support. However, the wall of the feed line may also be provided with a special undulating profile that imparts the necessary bending properties, and at the same time kink resistance, to the tube.

To allow the filling of the anorectally placed balloon to be adapted as precisely as possible by a closed control loop, a pressure-receiving element 9 is integrated into the balloon 5, preferably in the region of the rectal segment of the device. In the case of an electronic sensor component, the element 9 merges into a cable 9a that establishes the connection to the extracorporeal controller unit 3. Pressure-receiving components that are convertible into an electronic signal are likewise conceivable which, with or without their own integrated energy source, conduct the pressure prevailing in the balloon to the controller of the controller unit.

As an alternative to electronic sensors, a separate tube-like channel 9b may be integrated into the device, the channel being connected to a pressure-receiving sensor 9c outside of the patient and in turn communicating with the controller via a cable connection 9d.

The connection of the patient-side unit 2 of the device to the extracorporeal controlling mechanism 3, in particular the connection for the supply and discharge of volume to the balloon, takes place in each case via specifically designed connector components that rule out mix-ups.

The controller 3 has a programmable control unit C that is provided with appropriate control algorithms. It has a terminal function T for the input of control parameters by the user. In addition, it contains a module that is preferably made up of two separate pressure- and/or flow-controlling valve units Vi for the inflow and Vo for the outflow. The controller may also contain a module M, situated upstream from the respective valve units, with a reservoir function and/or pump function and/or a connection to an external pressure or negative pressure source.

Figure 1A:
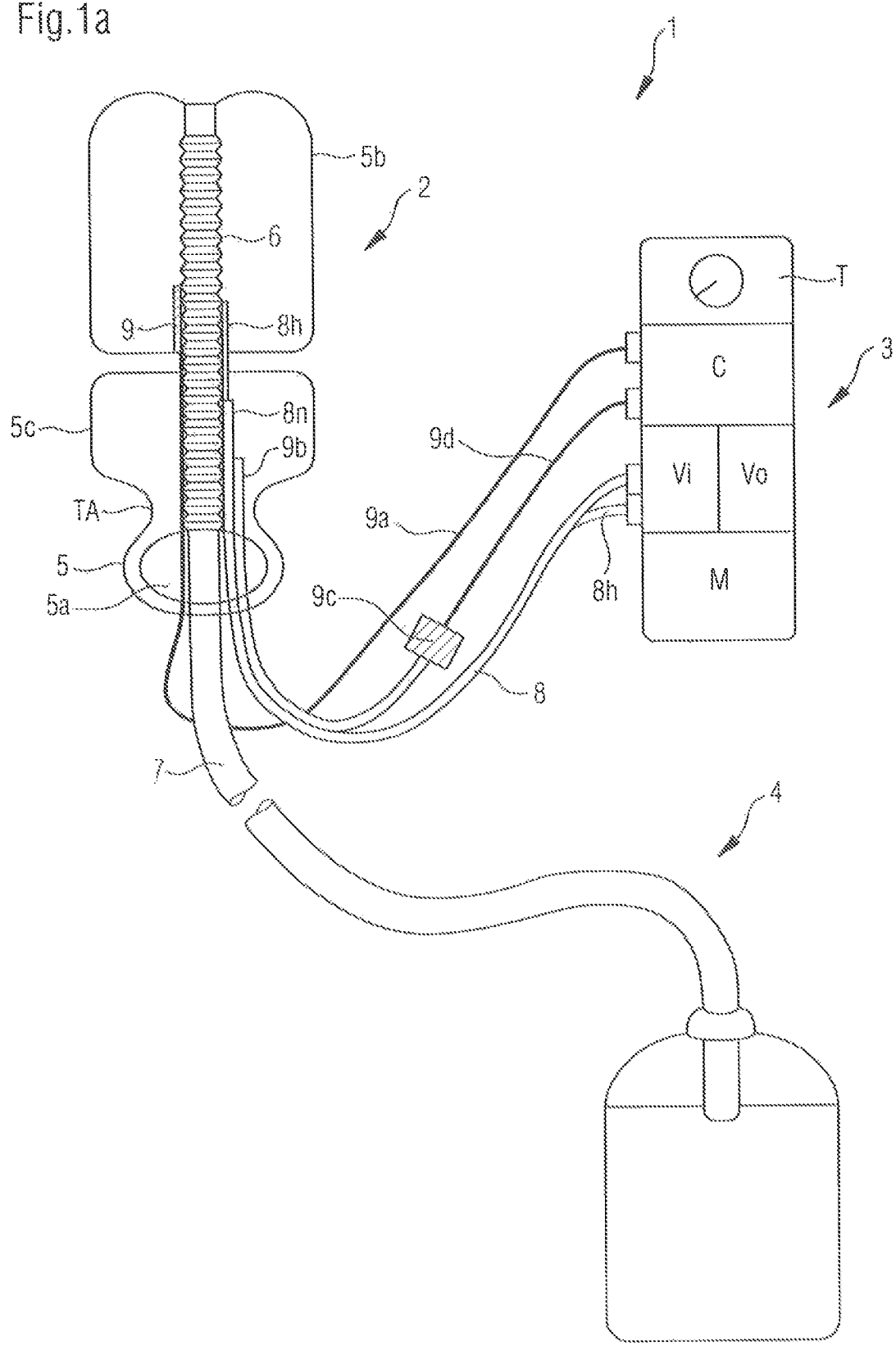
FIG. 1a shows one embodiment of the invention having sequentially arranged, separately fillable balloon segments.

FIG. 1a shows a particular axially segmented embodiment of the rectal or rectosigmoidal balloon body, by means of which the tamponading sealing device in the region directly exposed to the anastomosis may be filled in a particularly adaptive and perfusion-protecting manner, i.e., with particularly low pressure values that maintain the perfusion of the anastomosis. Pressure-related infarctions in the region of the anastomosed ends of the intestine may thus be optimally prevented. The embodiment thus has a relatively high-pressure segment 5b and a relatively low-pressure segment 5c. In the low-pressure segment, it is thus possible to set, for example, tamponading pressures of only 5 mbar above the organ internal pressure prevailing in the resection region.

The low-pressure segment 5c preferably extends through the anal canal and encloses the preanal abutment element 5a. The high-pressure segment 5b is positioned distally with respect to the low-pressure segment. Its task is to establish a sealing function in a section of the intestine at a distance from the anastomosis in the oral direction. The vascular perfusion is unimpaired in this portion of the intestine, and thus allows higher filling pressures that optimize the sealing efficiency of the balloon tamponade.

The two segments 5c and 5b in the region of the contact of their balloon shoulders are formed in such a way that they rest against one another with the smallest possible upper and lower shoulder radii, so that pocket-like spaces for the collection of intestinal contents between the balloon segments are avoided.

The segments 5b and 5c have their own separate feed lines 8h and 8n, respectively. The associated controller 3 is supplemented with appropriate additional inputs, valve units, input and control functions, and outputs for the second balloon segment to be controlled. In the preferred design, the device is equipped with an electronic pressure sensor or a pressure-receiving unit, and a unit that makes a conversion into an electrical signal, in the high-pressure segment and in the low-pressure segment.

FIG. 1b shows two variants of a design that is modified with respect to the embodiment according to FIG. 1, in which the diameter of the balloon segment 5d exposed to the anastomosis AS is reduced to approximately the diameter of the interior shaft tube 6. The remaining gap space between the segment 5d and the diameter of the shaft tube is 3 to 10 mm, preferably 3 to 5 mm. In the region of the anal canal, the balloon segment 5d merges into a diameter corresponding to the open, relaxed, largely atonal anal canal, i.e., has a diameter that exceeds same by up to 50%, preferably up to 25%. The balloon segment 5d may surround a preanal abutment element 5a, but may also terminate preanally in flush alignment with the external opening of the anal canal, where it may merge into a preanally applied film-like adhesive fixing, or may be joined to such, preferably without forming an intermediate space.

As is apparent in FIG. 1b at the half of the catheter 2 illustrated on the right, within the scope of this embodiment the distal end-position balloon segment 5e may be connected to the proximal segment relative to this tapered segment 5d, and optionally also to the preanal segment 5a, in a continuous, freely communicating manner, so that constant pressure compensation is possible between all balloon segments 5a, 5d, 5e. The balloon segments 5a, 5d, 5e are all supplied only via one or more shared filling lines 8.

If the balloon is formed, for example, from PUR-based raw tube material via a blow molding process, greater wall thicknesses of the balloon envelope result in the segment 5d having a diameter that is tapered relative to the segment 5e, as the result of which a radial expansion of the envelope of the segment 5d near the anastomosis may be avoided, even with transient higher filling pressures.

In this design, the continuous balloon body in the anastomosis region AS develops no tamponading function lying flatly against the anastomosis, and prevents the perfusion-hindering direct contact of the balloon body with the anastomosed balloon ends. The tapered segment 5d also protectively encloses the shaft tube and prevents direct mechanical irritation of the suture area by the stool-conducting shaft tube, which has much thicker walls compared to the balloon body.

To allow wound secretions produced by the anastomosis to be discharged from the region of the tapered segment 5d, the device is provided with a special discharge line DL having draining action, and which receives wound secretions in the region of the anastomosis and extracorporeally discharges them via a tube line 7a.

With reference to the separated design of the balloon body shown in FIG. 1a, the proximal tapered segment 5d may also be structurally and functionally separate from the distal sealing segment. Such an arrangement is depicted in FIG. 1b at the left half of the catheter 2. There is no flow connection here between the distal or oral balloon segment 5e and the proximal or aboral balloon segment 5d, so that the respective pressures in the two balloon segments 5d, 5e may be separately specified and/or controlled. In particular, the pressure in the distal balloon segment 5e may then be set higher than in the proximal balloon segment 5d.

FIG. 1c shows one embodiment of the device having a special preanally fixing component, wherein instead of or in addition to an abutment element 5a, a film-like fastening FB is used which is flatly adhered to the perianal skin areas PH of the patient. The film fixing is preferably composed of thin-walled thermoplastic film made of polyurethane, as used, for example, for fixing wound dressings or for direct skin protection. The film may be consistently flat, or may also be coated only in sections with an adhesive, for example also a PUR-based, strongly adhesive gel that allows sufficient adhesion to the skin surface over an application period of several days. The fastening film is preferably designed with a double-winged, propeller-like shape, the wing faces each being adhesively bonded to the inner surfaces of the anal fold.

FIG. 2 shows the patient-side unit 2 of the device in transanal positioning in the body of the patient. The circularly extending anastomosis AS is situated above the anal canal TA. The balloon element 5 extends from the preanal area PA via the anal canal TA and through the rectum R, optionally into the region of the sigma S. If a contraction of the sigma, the rectum, or also the anus occurs, the preferably gaseous filling medium or the air filling in the balloon element is compressed, causing the pressure to increase in all other segments of the tamponading balloon body. This pressure change is recorded by the sensor 9, and prompts the control unit C to open the valve Vo. The valve continuously releases volume from the balloon during the action of force on the balloon body, so that a certain setpoint pressure in the balloon, set by the user, remains as constant as possible. If the tonus of the contraction diminishes and the intestinal lumen opens, the valve Vi correspondingly supplies volume to the balloon in order to once again maintain the setpoint pressure. Due to this interaction, a peristaltic contraction of the rectosigmoid colon may be compensated for in such a way that on the one hand, the balloon filling pressure over the course of the contraction does not generate critically high pressure values endangering the anastomosis. On the other hand, it is ensured that the filling medium in the balloon is not compressed in the manner of a bolus in front of the contraction wave, and the entire device and intestinal contents are not expelled from the rectum, but, rather, the device remains in the specific tamponade position necessary for its function.

In one preferred embodiment of the device, the pressure-receiving electronic sensor 9 is mounted on the surface of the shaft tube in the region of the anastomosis. The electronic sensor thus ensures that critical pressures are measured as precisely as possible and recorded with the smallest possible time delay. To detect a perfusion-reducing effect of potentially critical pressures on the vascular bed in the region of the anastomosed ends of the intestine, a sensor 10 that operates with infrared diode light may be fixed to the shaft tube at the level of the anastomosis to be protected, and detects a certain segment K of the anastomosed intestine, and in this segment or in a conical section of the intestinal wall generates an electronic signal that is usable in a plethysmographic method. The signal allows detection of the wave-like capillary blood flow in the region of the wound, as well as recognition of relative changes and stoppage of perfusion and provision of appropriate alarms. Alternatively or additionally, the device having a tamponading sealing action may be equipped with one or more light sources 10a in the region of the anastomosis, mounted inside the balloon body, preferably on the shaft tube; their light quality and power may be adjusted in such a way that the blood-filled vessels in the anastomosis region have sufficiently good contrast to allow the surgeon to make a direct assessment of the local perfusion in situ, within the surgical site. In addition, special light may be used which illuminates substances that are intravascularly supplied to the patient, as is customary, for example, in the representation of blood vessels using fluorescent angiography.

To ensure a particularly efficient tamponading seal of the intestinal lumen that dynamically adapts to the forces prevailing at a given moment in the pelvis and abdomen of the patient, with the lowest possible temporal latency, the balloon 5 extends into the anal canal, and in the preferred embodiment, over the entire longitudinal extension of the anal canal up to the external opening of the anus. As an optional structural variant, the balloon body extending through the anus expands preanally as a spherically discoid compartment, for example, and completely or only partially encloses or surrounds the retention element 5a. The diameter of the balloon 5 in the transanal segment TA is preferably selected during manufacture in such a way that it can follow the lumen of the anal canal to be sealed at that moment, without the need to stretch the wall of the transanal balloon segment, which may be ensured by appropriate residual dimensioning of the diameter in this balloon segment. For preformed diameters of 20 to 35 mm in the balloon segment TA, the expected fluctuations in the diameter of the anal canal, from the folding in of the residually dimensioned balloon wall that results in situ inside the anal canal, may thus be compensated for in a sufficiently sealing manner. The force that presses the balloon envelope with a sealing function close against the mucosa of the anal canal corresponds to the particular force that is rectosigmoidally absorbed by the balloon body. If the transanal balloon diameter exceeds the particular diameter of the anus, a transanal sealing pressure in the described embodiment, continuously corresponding to the rectosigmoidal pressure, may be generated. A force-intensive expansion of the balloon envelope for the sealing closure of the anal canal may thus be avoided until the transanally turned-in residual reserve folding completely ends.

As a retention element 5a, a balloon component is preferably used whose formed balloon dimensions are adapted for mechanically effective retention or securing of the device upstream from the anus. The element is made, for example, of a material having only limited volume expandability. It has a diameter of 25 to 50 mm, preferably 30 to 40 mm. The balloon 5a is preferably manufactured from a PUR having a Shore hardness of 90A to 95A or 55D to 65D. Alternatively, it is filled with a gaseous or also liquid medium, the filling volume being dimensioned in such a way that the balloon is only partially filled and goes into a slack, undistended state, i.e., lies against the anus as a pliant, soft body, and goes into a taut state, then into a state having retaining action, only upon an axial movement of the device toward the patient. Alternatively, the retention element may be made of a gel-like or foam-like solid material.

In order to center the distal opening of the stool-receiving and -conducting shaft tube 6 and hold it axially oriented toward the upstream intestinal lumen and keep it open, the distal radius of the balloon 5 in the region of the transition 6a to the shaft tube may be stabilized by a circular, film-like reinforcement 6b that is for example flatly adhered to the balloon body. To avoid possible dislocation of the distal drainage opening due to portions of the balloon wall temporarily lying across the opening of the shaft tube, the distal shaft end may be provided with an olive- or mushroom-shaped element that extends beyond the front balloon radius.

The shaft tube 6 is preferably made of a PUR having a Shore hardness of 80A to 95A or also 55D to 60D. The shaft tube is preferably provided with an undulating profile that imparts the tube with axial flexibility that preserves the draining tube lumen, wherein bends of the tube axis by 90 to 135 degrees that are as tension-free as possible are possible. The tube has a diameter of 12 to 20 mm, preferably 14 to 16 mm. Depending on the material durometer used, the wall thickness is approximately 0.3 to 0.8 mm. The undulation amplitude is approximately 0.8 to 2.0 mm, and the wavelength is approximately 1 to 3 mm, preferably 2 to 2.5 mm.

The undulation of the tube profile assists the spontaneous straightening from a radially and axially deformed state under load into the particular initial state that is preformed during manufacture. The undulation of the tube also allows an overall advantageous, particularly thin-walled, film-like design of the tube, and assists with its spontaneous, elastic axial unwinding or prevents lumen-closing axial torsions. In the region of the retention element 5a the shaft tube preferably obtains no undulation, but instead is supplemented, with preservation of the lumen by a sleeve-like, cylindrical reinforcement 6c, for example.

Figure 2A:
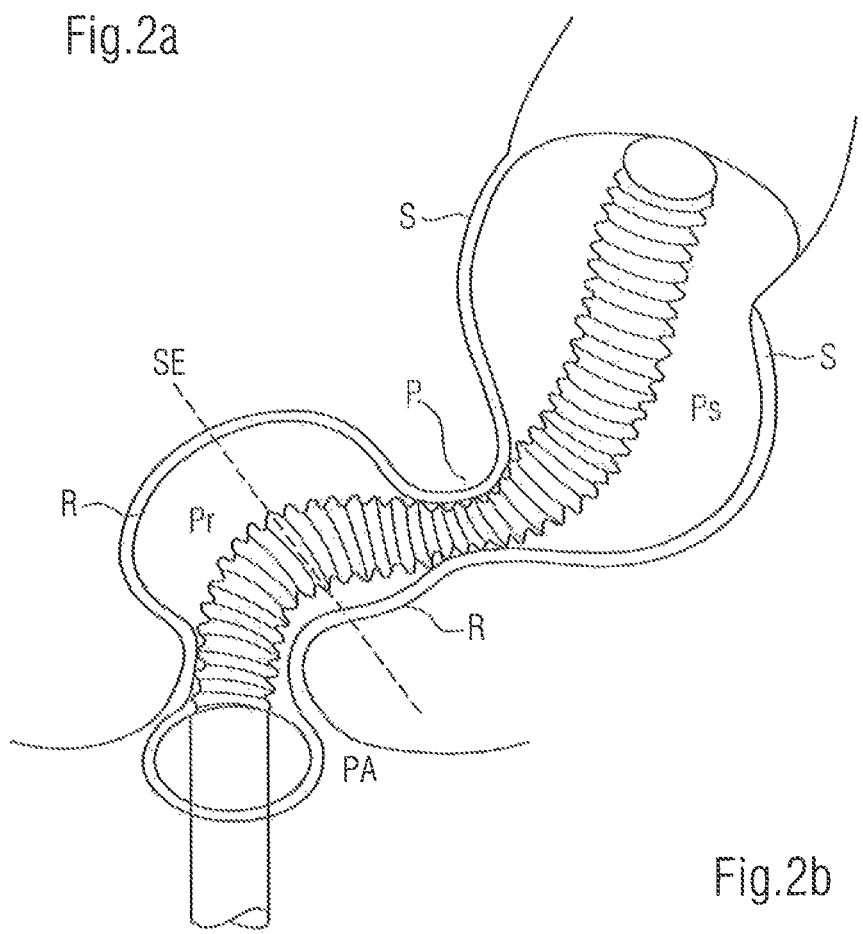
FIG. 2a shows the balloon body of a device according to the invention in the state of a sigmorectal peristaltic contraction.

FIG. 2a shows the device described in FIG. 2 in situ, in combination with a peristaltically occurring contraction P of the intestinal wall acting in the region of the rectosigmoidal transition between the rectum R and the sigma S.

The sigmoidally situated balloon section above the contraction remains closely pressed against the intestinal wall in a tamponading sealing manner. The pressure Ps in the balloon segment above the contraction that propagates to the anus in an undulating manner corresponds to the pressure Pr below the contraction wave. The invention ensures that in both balloon portions, i.e., above and below the contraction wave, a specified tamponade pressure is maintained, and the wall of the balloon body reliably remains sealingly pressed against the wall of the intestine.

Figure 2B:
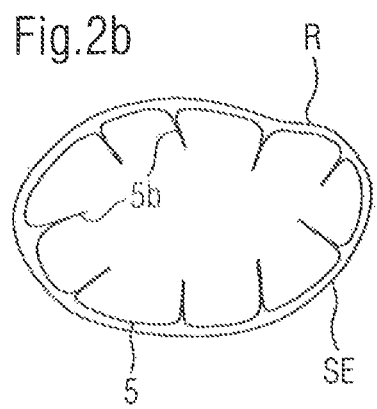
FIG. 2b shows a transverse section plane of the rectum to illustrate the folding behavior of a residually dimensioned balloon positioned in the rectum.

FIG. 2b illustrates the section plane SE through the rectum R. The balloon 5, residually dimensioned in diameter, folds into a reserve fold 5b. The fold ensures that the balloon wall lies close against the particular cross section of the intestinal lumen without tension, thus maintaining the physiological state of the intestine.

The balloon 5 is preferably made of a thermoplastic PUR having a Shore hardness of 85A to 95A, preferably 90A to 95A. In the region of the rectum and the sigma it has a formed diameter of 50 to 100 mm, preferably 50 to 70 mm. The wall thickness of the balloon in the rectosigmoidal region is 7 to 35 µm, preferably 10 to 20 µm. The diameter of the balloon 5 is preferably dimensioned with respect to the diameter of the rectum or the sigma in such a way that the balloon envelope folds into a reserve fold 5b during the placement in situ.

Figure 2C:
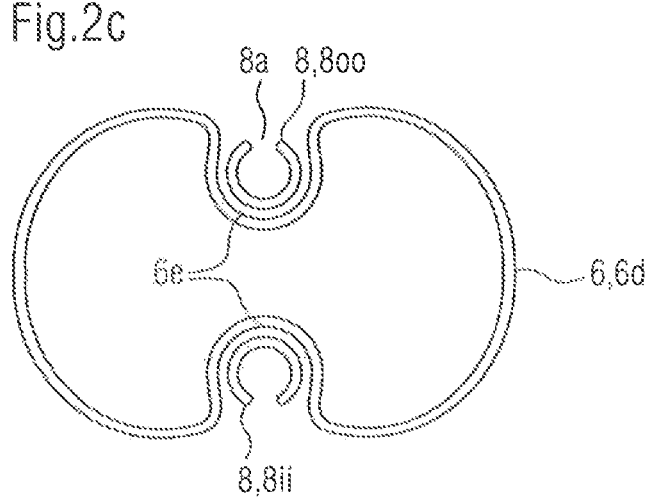
FIG. 2c shows a special design of a shaft tube that carries the balloon, having supplying and/or discharging tube lines, embedded in the tube profile, for filling the catheter balloon and for stabilizing the rectosigmoidal position of the balloon tamponade.

FIG. 2c shows a particular cross section 6d of a tube element 6 provided with an undulatingly corrugated profile that stabilizes the lumen. At one, but preferably two, mutually opposite positions in the tube circumference, the tube cross section has trough-like depressions 6e, in which the feed lines 8 that fill the balloon 5 and that are fixedly or also detachably connected to same are embedded. The feed lines have a series of openings 8a over the entire length of the shaft tube carrying the balloon.

The feed lines 8 embedded in the depressions 6e may also contribute to the axial reinforcement or stabilization of the shaft tube, so that even in the event of a peristaltic contraction of the colon that extends beyond the device, the shaft tube does not axially kink or fold in, or perhaps fold over axially at an angle of greater than 90 degrees, but instead follows the course of the intestinal windings. The feed lines are preferably made of a material having a greater Shore hardness and/or greater wall thickness than the materials used for the shaft tube.

With reference to FIG. 1a, which illustrates the sequentially arranged balloon segments 5b, 5c that are completely separate from one another, one of the two feed lines 8 may lead to the distal balloon segment 5b, and the other may lead to the proximal balloon segment 5c, filling each separately.

Figure 2D:
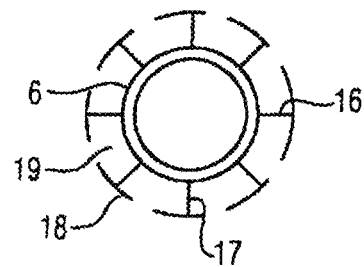
FIG. 2d shows a further embodiment of a shaft tube.

FIG. 2d shows a cross section of a shaft tube 6 of the device having a particular design. The tube is surrounded by a concentrically arranged outer sleeve tube 16, which remains spaced apart from the circumference of the shaft tube 6 via a noncollapsible or only partially collapsible spacer element 17, thus producing a certain nonclosable space 19 between the tube layers. In the event of a peristaltic contraction, filling medium from portions of the balloon 5 under peristaltic load is received into this space through numerous sieve-like openings 18 in the sleeve tube and across the space 19, and displaced into the sections of the balloon situated above the contraction wave, which are already released once again from the contraction. The sleeve tube 16 preferably extends over the entire rectosigmoidal extension of the shaft tube. The sleeve tube provides for local redistribution of filling medium inside the balloon, thus reducing potential peak pressures in the balloon regions below the contraction wave that endanger the anastomosis, or helps prevent the device from being pushed out of the transanal position by a bolus-like compression of filling medium in the rectal segment of the balloon.

FIG. 2e shows two variants of a tamponading balloon body 5, which over the longitudinal axis of the balloon body 5 is provided with completely circular or also partially circular constrictions 5c that incise the balloon along its circumference. The incising constrictions 5c improve the placement properties of the balloon in situ, in particular in the region of a flexure or bend of the colon, as typically found in the sigmoid of the colon. In the filled state of the balloon, the incising constrictions 5c reduce its tendency to spontaneously align over its longitudinal axis, and thus impart advantageous axial flexibility and bendability to the filled balloon. Elastic restoring forces that axially align the balloon are largely avoided by placement of a singly or multiply incised balloon body 5. In particular, the multiply constricted balloon body 5 with circular constrictions of at least 180 degrees of the balloon circumference at intervals of 3 to 4 cm improves the compatibility with the colon and the wearing comfort of the patient.

A variant is apparent on the right side of FIG. 2e in which the incising constrictions 5c do not extend to the central shaft tube 6, but instead freely end at a distance therefrom, so that the balloon 5 is not divided into individual chambers, and may be jointly filled or emptied through a single filling tube 8.

In contrast, another variant is illustrated on the left side of FIG. 2e, in which the incising constrictions 5c extend completely to the central shaft tube 6, where they are fixed in an airtight manner. In this case the balloon 5 is thus divided into multiple chambers lined up in a row along the shaft tube 6. Since these chambers do not communicate with one another, they must be individually filled, which may take place via a filling line 24 that has an opening 25 in each chamber. This embodiment also has the advantage that due to the filling line 24, pressure compensation between various chambers of the balloon 5 is possible at all times, in particular in the event of a peristaltic contraction. To guarantee this compensation flow, the filling line 25 may be inserted into a depression extending longitudinally along the shaft tube, or may have some other, in particular radially acting, reinforcements.

Figure 3:
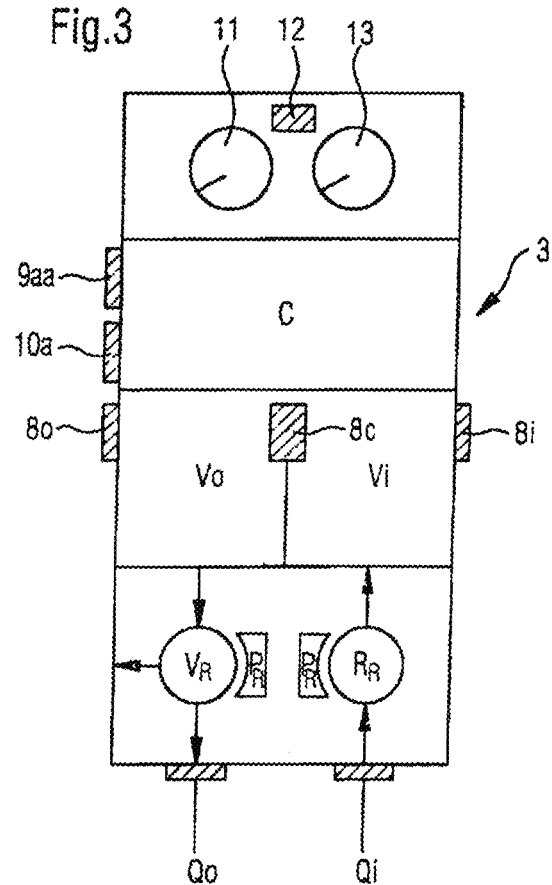
FIG. 3 shows a controller unit according to the invention in a schematic illustration.

FIG. 3 shows an example of the design of the controller unit 3 in detail. The programmable control unit C provided with a control algorithm has a socket-like connection 9aa for attaching the cable connection to the pressure sensor 9 mounted inside the balloon. Alternatively or in combination, the controller has a cable with an end-position pressure transducer 9c, and for the case of measuring the tamponade pressure, has a separate measuring tube 9b that is integrated into the device and whose proximal end is connected to the pressure transducer. The connection takes place as close as possible to the device, preferably not more than 20 cm from same.

The valve units Vi and Vo are preferably made up of piezoelectrically operating valves that allow a very precisely adjustable regulation as well as sufficiently high flows. Preferably two valves are installed, the one valve Vo allowing volume to flow out of the balloon. The controller may speed up removal of volume via an integrated mechanism $V_R$ that generates a negative pressure or an externally generated negative pressure Qo.

The supplying of volume to the balloon via the valve Vi likewise takes place based on a pressure gradient provided upstream from the valve, the filling medium in a reservoir $R_R$ being raised to a certain pressure level to be maintained therein, for example using an integrated pump $P_R$. Alternatively, the required pressure gradient may be established using an external source Qi.

The control unit also has a manual adjustment function 11 for the therapeutically necessary filling pressure to be continuously maintained in the balloon, and an adjustment option 13 for adjusting the particular controlling flow or the speed of the pressure compensation or the displacement of filling medium to the patient and/or from the patient. The unit also has an alarm function 12 which displays pressure values inside the balloon that exceed the selected tamponade pressure.

The inlet 8o from the balloon 5 to the controller valve Vo and the outlet 8i from the controller valve Vi to the balloon 5 may be combined into a single lumen 8, using a Y piece 8c. Alternatively, the lines to and from the proportional valves may be separately led to the catheter device, and in the case of two separate feed line tubes 8ii and 8oo integrated into the tube casing at that location, may each be attached to the corresponding tube lines. In the control, volume may thus be simultaneously supplied to and discharged from the balloon.

FIG. 3a shows a simplified controller unit 3a made up of a piezoelectrically operating valve Voi that moves volume to the tamponading balloon and also discharges volume from same. The connection to the catheter takes place via a single-lumen tube connection 8 and a connector 8oi. Situated upstream from the valve, toward the patient, is an electronic pressure-measuring component 21 that continuously detects the pressure in the balloon and supplies it to the control unit C. The controller unit 3a has no connection or readout function for a pressure that is electronically measured in the balloon. Either a pressure reservoir $R_R$ that is integrated into the appliance, or an external pressure source Qi that keeps filling medium in a pressure range of 1 to 2 bar, for example, is situated upstream from the valve on the side facing away from the patient. The piezo valve reduces this pressure to approximately 10 to 20 mbar sealing pressure in the balloon. If the pressure in the balloon increases, it is measured by the component 21. The valve then discharges filling medium, which follows the particular gradient, to the surroundings via an opening 20. The unit likewise has an adjustment option 11 for the setpoint pressure, and an option 13 for adjusting the particular volumetric flow to or from the balloon 5.

Figure 4:
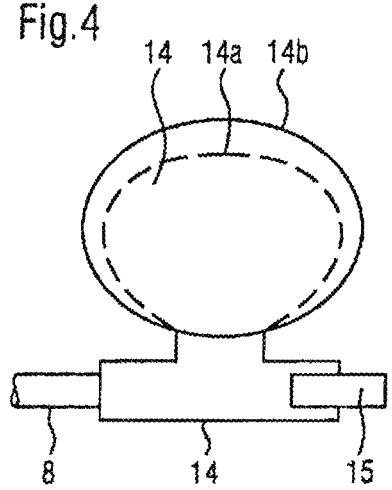
FIG. 4 shows a mechanically acting extracorporeal pressure source for ensuring an isobaric pressure profile in the tamponade balloon.

FIG. 4 shows a balloon-like reservoir 14 made of a material that is volume-expandable in a specific manner, and that when filled, preferably with air, goes into a specific mechanical expansion range in which filling medium may be received 14b into or discharged 14a from the reservoir balloon at constant pressure. The balloon thus stays "isobaric," in a manner of speaking, due to a specific filling pressure defined by the specific volume expandability of the balloon. The balloon is preferably made of an isoprene-like or TPE-based material. It is thus in open communication with the rectosigmoidally placed tamponade balloon 5, both toward and away from the patient, via the feed line 8. The isobaric volume range of the reservoir is preferably set during manufacture, via the specific material selection and the dimensioning of the controlling balloon component, in such a way that isobaric pressure plateaus of 10 to 30 mbar result, depending on the technical design of the balloon. The reservoir balloon is acted on by a simple filling valve 15 in the isobaric expansion range.

FIG. 4a shows a portable embodiment 22 of an isobarically controlling volume reservoir designed corresponding to FIG. 4. The reservoir has a cup-like space 22a that is closed by a cover-like structure 22b. The space protectively accommodates a TPE-based balloon 14, for example, that is expanded from an unfilled, partially formed basic state 23a into a filled state 23b. The balloon is fixed to the cover 22b, and its interior space merges into the feed line 8 to the catheter balloon. The reservoir balloon is acted on with pressure by air via a one-way valve 23.

Moreover, the invention describes a method for postoperative patient care after application of a surgical end-to-end anastomosis in the region of the terminal colon, it being possible to dispense with a protective application of an artificial intestinal outlet (stoma), heretofore mandatory by necessity, for prevention of suture insufficiency, and instead a permanently placed, bypass-like drainage device being introduced into the lumen of the rectosigmoid colon, which receives liquid modified stool in an intestinal segment situated above, i.e., orally with respect to the anastomosis, via a tube-like discharging device, and conducts the stool through the anastomosed portion of the intestine and the adjoining anal canal into a stool-collecting container placed outside the body. The tube element, which receives the stool in the intestine and discharges it naturally through the intestine, is made of a flexible tube material that is bendable with as little tension as possible, and that under high enough radial load elastically collapses in a ribbon-like manner and/or elastically radially folds in singly or multiply, and when the load diminishes, straightens, once again in an elastic manner, into the profile of its particular manufactured state. In the preferred embodiment, the tube element has a structural design such that the transition from, for example, a circular diameter of the manufactured state into the elastically deformed state requires a certain initial force that must be overcome. If the particular force is overcome or a departure is made from the stable manufactured cross section of the tube, the further deformation or folding of the tube is possible with a force that is smaller relative to the initial force. A corresponding shaft mechanism may be produced or adjusted, for example via a coil- or ring-like undulating corrugation of the tube wall. The tube element as an essential component carries a preferably membrane-like thin-walled balloon body that is completely formed to the required working dimensions, and that extends from the upper, oral opening of the tube, via the aborally adjoining segments of the colon, through the anal canal of the patient, and into the directly preanal region, where it encloses an optional preanally retaining element, or directly aborally adjoins the preanal end of the balloon. The balloon body is preferably dimensioned in such a way that it corresponds to the diameter of the atonal colon or rectum or exceeds the atonal diameter thereof by up to 50%. Thus, during the filling with a filling medium using an extracorporeal control mechanism, no force-intensive expansion of the balloon envelope needs to be carried out to achieve a sealingly active tamponade or close fitting of the balloon to the wall of the intestine. Instead, the close fitting already takes place at pressure values that do not exceed, or exceed by only a few millibars, the physiological pressures prevailing within the intestine. The balloon envelope that is tamponaded in this way without tension is filled with a preferably gaseous medium or acted on by tamponading pressure by the controlling, extracorporeal portion of the device in such a way that in response to the particular tonus of the intestine or its contraction state at that moment, a consistent filling pressure specified by the user results inside the balloon body, which ranges from approximately 5 to 30 mbar, for example, and maintains the capillary perfusion in the region of the ends of the intestine connected end-to-end, particularly critical in vascular terms, and therefore the force from the balloon acting transmurally on the vascular bed of the intestine does not cause critical reduced perfusion. To avoid peak pressures inside the balloon body, which may possibly result from peristaltic preservation of the intestinal segments resting against the balloon and which may jeopardize the integrity of the anastomosis, at the beginning of an exceedance of the setpoint value specified by the user, the controlling mechanism actively withdraws filling volume from the balloon or initiates its passive outflow from the balloon. A lumen constriction peristaltically extending across the intestine is thus compensated for while maintaining the setpoint pressure. After the particular action of force on the intraluminally placed balloon body that tamponades the lumen of the intestine diminishes, and an initial pressure drop thus occurs in the balloon, filling medium is once again supplied to the balloon by the controlling unit in such a way that the specified setpoint pressure is consistently maintained. The dynamic displacement of filling medium out of and into the tamponading lumen-closing balloon allows the catheter-like device to be stationarily held in the intestine, and allows the prevention of peristaltic expulsion or elimination of the device from the intestine, or allows holding the device in the position, extending across the anastomosis, that is necessary for its specific function.

As an alternative to a single, consistently cylindrically shaped balloon body, the colorectal tamponade may also be produced, for example, by two sequentially arranged cylindrical balloons, both balloon components having the same or approximately the same diameter, and both segments being individually fillable. For its primarily sealing function, the orally positioned balloon close to the opening has a higher setpoint pressure than the default, while a comparatively smaller pressure, with the greatest perfusion protection possible, prevails in the aborally positioned balloon exposed to the anastomosis.

In one preferred embodiment of the balloon body, its consistently one-part (oral) segment has a larger diameter than the aboral segment exposed to the anastomosis. Whereas the oral segment has primarily a sealing function, the portion of the balloon body adjoining aborally, which is exposed to the anastomosed segment, has primarily a protective function. A mechanically erosive effect of the shaft tube on the anastomosis is thus avoided. In addition, the segment does not exert direct pressure on the anastomosis, thus ensuring that secretions released from the suture may flow out into the lumen of the intestine unhindered and without resistance. The balloon envelope, whose diameter is reduced approximately to the dimension of the shaft tube, thus allows a certain intermediate space that can accommodate secretions and enables the passive discharge of secretions from that point. For this purpose, the segment is provided with a separate draining opening into the secretion-accommodating space, the discharge of the secretions accommodated in the suture area taking place via a separate tube line into a collection container placed outside the body. As an alternative to a continuous balloon body formed in this way, once again two separately fillable balloon compartments arranged in series are conceivable.

The control of the filling of the balloon body preferably takes place via two separately produced tube feed lines that are integrated into the circumference of the tube element via corresponding inlets and offset by 180 degrees. These tube feed lines are designed with regard to material type, wall thickness, and wall profile in such a way that they provide the necessary axial stability in the device that is colorectally placed in the patient, in order to ensure a continuous axial orientation of the shaft tube that follows the lumen of the intestine and prevents kinks and twists.

The control of the filling pressure takes place extracorporeally, using two conceptual types of mechanisms. As a particularly simple, purely mechanical design of the mechanism, the controller may be made of a special, volume-elastic balloon material which beyond a certain filling range or expansion range of its balloon wall keeps a filling medium at a certain defined pressure via mechanical expansion. The displacement of medium to or from the patient takes place in such a way that in the entire system acted on by filling pressure, a pressure results that corresponds to the tamponade pressure to be set, and that does not exceed this atraumatic, perfusion-maintaining pressure.

The volume reservoir which isobarically acts over a certain volume range is preferably used in the subsequent postoperative phase, after the healing process in the anastomosis region is well underway.

In the direct postoperative phase, electronically controlling mechanisms are preferably used which in the preferred case detect pressures that are already within the tamponading balloon envelope, using appropriate electronic sensor components, and which thus allow optimal control behavior, wherein the displacement of filling medium into and out of the tamponading balloon body follows a higher pressure gradient or differential pressure which speeds up the particular supply or discharge. The supply or discharge of medium is thus driven by pressures acting extracorporeally at the controller which exceed the atraumatic maximum pressure in the colorectal balloon body. Pressures of 100 to 200 mbar, for example, may be present at the input of the controlling valve. The control across such a pressure gradient allows optimal compensation to be made for flow resistances in the system filling the balloon. The control of the particular flows to and from the balloon preferably takes place using piezoelectrically driven valve units.

In electronically controlled systems, the user has the option to specify the setpoint pressure within relatively narrow limits, and to minimize the response time of the sealing tamponade by increasing the differential pressure between the intracorporeal balloon and the extracorporeal controller.

Subsequent to the end-to-end joining of the ends of the intestine, the device for the protective tamponade of an anastomosis suture is intraoperatively placed through the anus of the patient by the surgeon in such a way that the distal, stool-receiving end of the tamponade is positioned approximately 5 to 10 cm above the anastomosis.

The preanal retention balloon is subsequently filled and/or the device is gluteally fixed using an adhesive tape.

In the preferred type of application, the tamponading, stool-discharging drain in the initial phase of care is then connected to an electronic controller for about three to four days, for example, and preferably filled with air as filling medium, and a setpoint pressure of approximately 10 to 30 mbar, preferably 15 to 25 mbar, is set.

In the course of further care, a change is then made to a nonelectronic, mechanically acting, isobaric pressure controller. The isobaric pressure controller may be manufactured in portable form, and thus allows the patient optimal freedom of movement.

The efficiency of the tamponading seal is provided by an orally administered continuous stool-liquefying medication that maintains the stool in the thin liquid consistency necessary for the drainage over the required treatment period.

The treatment period is approximately 5 to 7 days total. The drain is then drawn through the anus, so that the application of a stoma may be prevented.

| List of reference numerals | |
|---|---|
| 1 | device |
| 2 | catheter |
| 3 | controller |
| 3a | controller |
| 4 | collector |
| 5 | balloon |
| 5a | retention element |
| 5b | high-pressure segment |
| 5c | low-pressure segment |
| 5d | balloon segment |
| 5e | balloon segment |
| 6 | tube |
| 6a | transition |
| 6b | reinforcement |
| 6c | reinforcement |
| 6d | cross section |
| 6e | depression |
| 7 | tube |
| 7a | tube line |
| 8 | feed line |
| 8c | Y piece |
| 8h | feed line |
| 8i | outlet |
| 8ii | feed line tube |
| 8n | feed line |
| 8o | input |
| 8oi | connector |
| 8oo | feed line tube |
| 9 | element |
| 9a | cable |
| 9b | channel |
| 9c | sensor |
| 9d | cable connection |
| 10 | sensor |
| 10a | light source |
| 11 | adjustment function, setpoint pressure |
| 12 | alarm function, pressure values |
| 13 | adjustment option, volumetric flow |
| 14 | reservoir |
| 14a | discharge |
| 14b | reception |

-continued

| List of reference numerals | |
|---|---|
| 15 | filling valve |
| 16 | sleeve tube |
| 17 | spacer element |
| 18 | opening |
| 19 | space |
| 20 | opening |
| 21 | component |
| 22 | embodiment |
| 22a | space |
| 22b | cover |
| 23 | one-way valve |
| 23a | basic state |
| 23b | state |
| 24 | tube |
| 25 | opening |
| AS | anastomosis |
| C | control unit |
| DL | discharge line |
| FB | fastening |
| K | segment |
| M | module |
| P | contraction |
| PA | preanal region |
| PH | skin area |
| Pr | pressure |
| Ps | pressure |
| Qi | source |
| Qo | negative pressure |
| R | rectum |
| S | sigma |
| SE | section plane |
| T | terminal function |
| TA | anal canal |
| Vi | inflow valve un |
| Vo | outflow valve unit |
| Voi | valve |

The invention claimed is:

1. A device (1) for the sealing protection, with tamponading action, of a surgically applied circular anastomosis (AS) between an oral end and an aboral end of the large intestine, in particular the rectum (R) or sigma(S), or some other suture or lesion present in this portion of the intestine, at the same time with a stool-discharging function through the segment (AS) of the intestine that is anastomosed, injured, or treated surgically or via some other intervention, and with subsequent passage of the stool through the anal sphincter (TA), characterized by at least one thin-walled balloon body (5), formed completely to its working dimensions during manufacture and made of a material with low volume expandability, for placement in the region of the anastomosis (AS) in such a way that a distal balloon end or a distal balloon segment (5b) of the at least one balloon body (5) is situated orally with respect to the anastomosis (AS), the balloon body (5) enclosing a flexibly and/or elastically deforming tube element (6) that passes through the balloon body (5) from the distal balloon end or the distal balloon segment (5b) to a proximal end or a proximal balloon segment (5c) of the at least one balloon body (5), where the tube element (6) is connected or connectable to an extracorporeal tube (7), spontaneously elastically straightens from an axially deformed state into an initial state preformed during manufacture and has a structural stability sufficient to allow a position, determined by a positioning relative to the anus, to be passed on to the distal balloon end or distal balloon segment (5b) of the at least one balloon body (5, 5b, 5c), and, under high enough radial load, elastically collapses from a profile preformed during manufacture into a radially deformed state, but when the load diminishes, the tube element (6) elastically returns into the profile preformed during manufacture, the balloon body (5, 5*b*, 5*c*) being connected to an apparatus that controls the supply and discharge of a filling medium to and from at least a portion of the balloon body (5, 5*b*, 5*c*) in such a way that in the tamponading balloon body (5, 5*b*, 5*c*), a lowest possible filling pressure necessary for the sealing tamponade of at least a portion of the intestine distally and/or orally with respect to the anastomosis, but also a pressure that is sufficient to continuously compensate for mass movements of the abdomen and in particular peristaltic contractions of the intestine, is continually maintained, so that the balloon body (5) is configured to effect consistent tamponading sealing contact with the intestinal wall, and critically high back pressures within the balloon body (5, 5*a*, 5*b*, 5*c*) that endanger the integrity of the anastomosis (AS) are avoided.

2. The device (1) according to claim 1, characterized in that the portion of the balloon body (5) is configured to extend into the colon so as to fill at least the rectum of the patient.

3. The device (1) according to claim 1, characterized in that a shaft of the tube element (6) is configured to follow the windings of the rectosigmoidal intestine with as little tension as possible, and carry the balloon body (5, 5*a*, 5*b*, 5*c*).

4. The device (1) according to claim 1, characterized in that a shaft of the tube element (6) is flexibly bendable, but has sufficient inherent rigidity to resist kinking or bending by more than 90°.

5. The device (1) according to claim 1 characterized in that a shaft of the tube element (6) is configured such that when the shaft of the tube element (6) is disposed in the region of the anus or in the region of a transanal balloon segment (TA), the shaft of the tube element (6) is able to radially fold in and straighten in an elastic manner.

6. The device (1) according to claim 1, characterized in that a diameter of the balloon body (5, 5*a*, 5*b*, 5*c*) in a freely unfolded state thereof is configured to correspond to a rectosigmoidal diameter of the respective freely unfolded, completely atonal rectum (R) and/or sigma(S), or is configured to exceed an estimated rectosigmoidal diameter and thus has a residual dimensioning.

7. The device (1) according to claim 1, characterized in that the proximal end of the balloon body (5, 5*a*, 5*b*, 5*c*) is configured to be situated orally with respect to the anastomosis (AS).

8. The device (1) according to claim 1, characterized in that the proximal end of the balloon body (5, 5*a*, 5*b*, 5*c*) is configured to be situated aborally with respect to the anastomosis (AS).

9. The device (1) according to claim 1, characterized in that the proximal balloon segment (5*c*) of the balloon body (5, 5*a*, 5*b*, 5*c*) is configured to extend in the region of the anastomosis (AS) and/or over the anastomosed portion of the intestine in the aboral direction, and/or into the anal canal or through the anal canal.

10. The device (1) according to claim 9, characterized in that the proximal balloon segment (5*c*) of the balloon body (5, 5*a*, 5*b*, 5*c*) has a smaller diameter than the distal balloon segment (5*b*), orally with respect to the anastomosis (AS).

11. The device (1) according to claim 9, characterized in that a tube line (7*a*) for drainage of wound secretions is situated in or opens (DL) into the region of the proximal balloon segment (5*c*) of the balloon body (5, 5*a*, 5*b*, 5*c*).

12. The device (1) according to claim 9, characterized in that the balloon body (5, 5*a*, 5*b*, 5*c*) is divided between the distal balloon segment (5*b*) and the proximal balloon segment (5*c*).

13. The device (1) according to claim 12, characterized in that the distal and proximal balloon segments (5*b*, 5*c*) do not communicate with one another, and therefore are adjustable or controllable an internal pressure within the distal balloon segment (5*b*) on the one hand and to a different internal pressure within the proximal balloon segment (5*c*) on the other hand.

14. The device (1) according to claim 13, characterized in that the internal pressure within the distal balloon segment (5*b*) is greater than the internal pressure within the proximal balloon segment (5*c*).

15. The device (1) according to claim 1, characterized in that the balloon body (5, 5*a*, 5*b*, 5*c*) has a transanal balloon segment (TA) that is configured to adjoin a rectally placed portion of the balloon body (5) or the proximal balloon segment (5*c*).

16. The device (1) according to claim 15, characterized in that the transanal balloon segment (TA) is configured to be positioned or positionable inside the anal canal, and the balloon body (5) is configured to continue through the anal canal.

17. The device (1) according to claim 15, characterized in that the transanal balloon segment (TA) or a tapered middle region (TA) of a dumbbell-shaped balloon body (5, 5*a*, 5*b*, 5*c*) has a diameter that corresponds to or exceeds a fully open anus.

18. The device (1) according to claim 15, characterized in that the transanal balloon segment (TA) or a tapered middle region (TA) of a dumbbell-shaped balloon body (5, 5*a*, 5*b*, 5*c*) is designed in such a way that an advantageous radial folding-in of a residual envelope wall, in excess of the diameter, results when the anal sphincter is partially open in the transanal balloon segment (TA).

19. The device (1) according to claim 15, characterized in that, when disposed preanal to the anus, the balloon body (5, 5*a*, 5*b*, 5*c*) is configured to expand into a spherical or discoid-shaped preanal segment (5*a*).

20. The device (1) according to claim 19, characterized in that a separately fillable inner balloon having an anchoring action or an abutment element, with a corresponding anchoring action is situated inside the preanal balloon segment (5*a*).

21. The device (1) according to claim 19, characterized in that the balloon body (5, 5*a*, 5*b*, 5*c*) in the preanal segment has an additional retention element (5*a*), in particular a thickened element, that protects the balloon body from sliding into the intestine of the patient.

22. The device (1) according to claim 20, characterized by a flatly adhering fixing element in the region of the preanal balloon segment (5*a*) for the purpose of fixing, with the action of an abutment, the balloon body (5, 5*a*, 5*b*, 5*c*) to the perianal skin.

23. The device (1) according to claim 1, characterized by the balloon body (5, 5*a*, 5*b*, 5*c*) being configured to assume a dumbbell shape when the balloon body (5, 5*a*, 5*b*, 5*c*) is disposed in the region of the anus of the patient, a tapered middle region (TA) of a dumbbell-shaped balloon body (5, 5*a*, 5*b*, 5*c*) being placeable in a transanal position in the anal canal in order to fix the balloon body (5, 5*a*, 5*b*, 5*c*) in the intestine of the patient.

24. The device (1) according to claim 1, characterized in that peristaltic contractions of the portions of the intestine that are exposed to the sealing tamponading balloon body are compensated for by adapting the balloon filling volume, and thus during the course of the peristaltic contraction a tamponading or sealing setpoint filling pressure specified by the user is maintained in the tamponading balloon body (5, 5a, 5b, 5c), or transient, critically high filling pressures are avoided.

25. The device (1) according to claim 1, characterized in that an intracorporeal pressure compensation and/or a displacement of a balloon filling volume between various balloon segments (5a, 5b, 5c) is made possible via an intracorporeal flow connection between various regions of the tamponading balloon body (5, 5a, 5b, 5c), in particular in the region of a shaft of the tube element (6).

26. The device (1) according to claim 1, characterized by flow channels (19) that extend in the region of a shaft of the tube element (6) of the balloon body (5, 5a, 5b, 5c) and that communicate with different regions of the balloon body (5, 5a, 5b, 5c), thus creating a flow connection between various regions of the balloon body (5, 5a, 5b, 5c) to allow an intracorporeal pressure compensation and/or a displacement of a balloon filling volume between various balloon segments (5a, 5b, 5c).

27. The device (1) according to claim 26, characterized in that flow channels (19) or filling lines (8) extending in the region of a shaft of the tube element (7) of the balloon body (5, 5a, 5b, 5c) are protected from closure, due to peristaltic contractions, via approximately radially extending regions of the shaft tube (7), in particular radial bars or spacer elements (17).

28. The device (1) according to claim 1, characterized in that one or more filling line(s) (8) extending in the region of a shaft of the tube element (6) of the balloon body (5, 5a, 5b, 5c) has/have multiple openings which and may thus communicate with different regions of the balloon body (5, 5a, 5b, 5c), so that a flow connection is created between various regions of the balloon body (5, 5a, 5b, 5c) to allow an intracorporeal pressure compensation and/or a displacement of a balloon filling volume between various balloon segments (5a, 5b, 5c).

29. The device (1) according to claim 1, characterized in that the balloon body (5, 5a, 5b, 5c) is connected via a tubular feed and discharge line (8) to an extracorporeal apparatus for regulating the supply and discharge of a filling volume.

30. The device (1) according to claim 29, characterized in that the tubular feed and discharge line (8) to and from the balloon body (5) has a large enough lumen that sufficiently high volume flows of the supplied and discharged medium are achieved, and such that balloon body (5) is configured so that the sealing contact of the balloon body (5, 5b, 5c) with respect to the intestinal wall is maintained in all segments of the sealing balloon body (5, 5b, 5c), in particular in the course of the contraction wave running from the colon to the anus.

31. The device (1) according to claim 29, characterized in that the tubular feed and discharge line (8) to and from the tamponading balloon body (5) has a cross section that corresponds to a circular cross section having a diameter of 2 to 4 mm, or of 4 to 6 mm.

32. The device (1) according to claim 30, characterized in that the balloon body (5, 5a, 5b, 5c) is fillable through a particular large-lumen, feed line (8) in the form of a tube from a machine controller (3) or from a volume reservoir (14) configured to be disposed outside the body.

33. The device (1) according to claim 1, characterized by a controller unit (3) configured to be disposed outside the body of the patient, having a pump unit and/or pressure unit as well as control valves (Vi, Vo, Voi), and a controller that acts on the control valves (Vi, Vo, Voi) and that is designed to fill and/or partially empty the tamponading balloon (5) with a filling medium in such a way that a filling pressure that is as small as possible and necessary for the sealing tamponade of the anastomosed portion of the intestine, and that continuously compensates for mass movements of the abdomen and in particular peristaltic contractions of the intestine, is maintained in the tamponading balloon body (5, 5b, 5c), so that the tamponading sealing contact of the balloon body (5) with respect to the intestinal wall is continually maintained.

34. The device (1) according to claim 1, characterized in that the filling takes place using a quick-controlling, high-flow valve system that is driven by an appropriately dimensioned pressure gradient and that actively conveys volume into the balloon and/or actively withdraws volume from the balloon.

35. The device (1) according to claim 34, characterized by particularly rapidly and precisely regulating, electronically controlled proportional valves that control the supplying and discharging of volume to and from the balloon body (5, 5a, 5b, 5c).

36. The device (1) according to claim 1, characterized by at least one pressure sensor, situated inside the balloon body (5, 5a, 5b, 5c) that is configured to tamponade the intestinal lumen or close off the intestinal cross section, which at least one pressure sensor continuously detects the particular prevailing filling pressure in the balloon (5) or balloon segment (5, 5a, 5b, 5c) in question.

37. The device (1) according to claim 36, characterized by multiple pressure sensors (9) situated in various sections or segments of the balloon body (5, 5a, 5b, 5c).

38. The device (1) according to claim 37, characterized by a controller for controlling the pressure in the region of the anastomosis (AS) to safe values below an upper limit value, in particular to avoid lesions in the region of the anastomosis (AS).

39. The device (1) according to claim 37, characterized by a controller configured for controlling the pressure in the balloon segment (5b), orally with respect to the anastomosis (AS), to values above a lower limit value, in particular to avoid leaks at that location with respect to the colon.

40. The device (1) according to claim 37, characterized in that the multiple pressure sensors (9) are situated in various sections or segments of the balloon body (5, 5a, 5b, 5c) for detecting the pressure in the region of the anastomosis (AS) itself and in the distal balloon segment (5, 5b).

41. The device (1) according to claim 36, characterized in that the at least one pressure sensor is situated inside the balloon body (5, 5a, 5b, 5c) in the region of the anastomosis (AS).

42. The device (1) according to claim 1, characterized by a pressure controller connected to the device (1), which during a peristaltic contraction of the terminal colon ensures a constant setpoint pressure in the tamponading balloon, specified by the user, which is necessary for protecting the anastomosis.

43. The device (1) according to claim 42, characterized in that peristalsis-related expulsion of the device (1) from the rectosigmoid or dislocation from its transanal position, necessary for a suture-protective function, is counteracted by appropriate control of the filling volume in the balloon body (5, 5a, 5b, 5c).

44. The device (1) according to claim 42, characterized in that when the peristaltic contraction subsides, or when the tonus of the intestinal wall decreases, with a corresponding dilation of the intestinal lumen, the pressure controller supplies the balloon body (5, 5a, 5e, 5b, 5c) with filling volume in a controlled manner in such a way that a setpoint pressure specified by the user, and thus the tamponading, protective effect of an envelope of the balloon body (5, 5a, 5b, 5c) on the anastomosed intestinal wall, is consistently maintained over the entire course of the contraction.

45. The device (1) according to claim 1, characterized by a portable appliance that is carryable by the patient, having an integrated pressure source or a pump device that compresses and keeps pressurized air in a reservoir container, and thus, via a controlling valve, over an appropriate differential pressure to a setpoint pressure to be achieved, ensures an appropriately high volumetric flow to the balloon and thus conveys volume into the balloon with little time delay.

46. The device (1) according to claim 1, characterized in that, in particular subsequent to the initial phase of care, the filling pressure within the tamponading device is maintained by means of a controller (3) or reservoir (14) that is controlled isobarically, i.e., over a differential pressure that does not differ significantly from a setpoint pressure.

47. The device (1) according to claim 1, characterized by an extracorporeal reservoir (14), in particular in the form of a reservoir balloon, that is wearable by the patient, and is connected or connectable via a filling line (8) to the device (1) having tamponading-draining action for controlling the balloon volume and balloon filling pressure.

48. The device (1) according to claim 47, characterized in that the reservoir (14) has a balloon that is volume-expandable and allows an essentially isobaric pressure profile over a certain expansion range of the wall of the balloon body (5, 5a, 5b, 5c) or the filling state of the balloon body (5, 5a, 5b, 5c).

49. The device (1) according to claim 47, characterized in that the filling medium is displaceable in both directions between the balloon body (5, 5a, 5b, 5c) and the controlling reservoir (14), without exceeding a maximum pressure in the overall system that is determined by the reservoir (14) via mechanical expansion.

50. The device (1) according to claim 47, characterized in that the isobarically controlling reservoir (14) has no valve that controls, damps, or determines the flow direction of the filling medium, but, rather, produces the necessary volume compensation between the tamponade in both directions via a feed line having a sufficiently large lumen, wherein an identical communicating pressure results in both compartments of the system in the resting state.

51. The device (1) according to claim 47, characterized in that the largely isobarically controlling volume reservoir (14) is installed in a protective container, and is portably carried by the patient.

52. The device (1) according to claim 1, characterized in that the removal of volume from the balloon body (5, 5a, 5b, 5c) takes place passively to the surroundings, or also actively into a vacuum placed in front of a valve or into a reservoir kept at an appropriate negative pressure.

53. The device (1) according to claim 1, characterized in that the portion of the balloon body (5) configured to extend into the colon so as to fill the rectum of the patient is also configured to fill the entire rectosigmoid, and/or encompasses portions of the intestine situated orally with respect to the rectosigmoid.

54. A method for the sealing protection, with tamponading action, of a surgically applied circular anastomosis (AS) between an oral end and an aboral end of the large intestine, in particular the rectum (R) or sigma(S), or some other suture or lesion present in this portion of the intestine, at the same time with a stool-discharging function through the segment (AS) of the intestine that is anastomosed, injured, or treated surgically or via some other intervention, and with subsequent passage of the stool through the anal sphincter (TA), characterized in that at least one thin-walled balloon body (5), formed completely to its working dimensions during manufacture and made of a material with low volume expandability, is placed in the region of the anastomosis (AS) in such a way that a distal balloon end or a distal balloon segment (5b) of the at least one balloon body (5) is situated orally with respect to the anastomosis (AS), the balloon body (5) enclosing a flexibly and/or elastically deforming tube element (6) that passes through the balloon body (5) from its distal end or balloon segment (5b) to a proximal end or a proximal balloon segment (5c) of the at least one balloon body (5), wherein the tube element (6) is connected or connectable to an extracorporeal tube (7), spontaneously elastically straightens from an axially deformed state into an initial state preformed during manufacture and has a structural stability sufficient to allow a position, determined by a positioning relative to the anus, to be passed on to the distal balloon end or distal balloon segment (5b) of the at least one balloon body (5, 5b, 5c), and, under high enough radial load, elastically collapses from a profile preformed during manufacture into a radially deformed state, but when the load diminishes, the tube element (6) elastically returns into the profile preformed during manufacture, the balloon body (5, 5b, 5c) being connected to an apparatus which controls the supply and discharge of a filling medium to and from at least a portion of the balloon body (5, 5b, 5c) in such a way that in the tamponading balloon body (5, 5b, 5c), a lowest possible filling pressure necessary for the sealing tamponade of at least a portion of the intestine distally and/or orally with respect to the anastomosis, but also a pressure that is sufficient to continuously compensate for mass movements of the abdomen and in particular peristaltic contractions of the intestine, is continually maintained, so that the tamponading sealing contact of the balloon body (5) with respect to the intestinal wall remains consistent, and critically high back pressures within the sealing balloon body that endanger the integrity of the anastomosis are avoided.

55. The method according to claim 54, characterized in that after a device (1) comprising the balloon body (5, 5b, 5c) is inserted in the proper transanal position by the surgeon, the balloon of the tamponading device (1) is connected to an extracorporeal control or regulation unit (3) that acts on the balloon (5, 5a, 5b, 5c) with a setpoint pressure that is selected by the user, and consistently maintains this pressure to compensate for peristaltic contractions and mass movements of the abdomen due to rapid supplying or removal of filling medium.

56. The method according to claim 54, characterized in that the balloon body (5, 5b, 5c) is connected via a tubular feed line and discharge line (8) to a controller unit (3) outside the body of the patient, the controller unit (3) having a pump unit and/or pressure unit as well as control valves (Vi, Vo, Voi), and a controller that acts on the control valves (Vi, Vo, Voi), the controller controlling the control valves (Vi, Vo, Voi) in such a way that the balloon body (5, 5b, 5c) is filled with a filling medium and/or partially emptied if necessary, in such a way that the lowest possible filling pressure necessary for the sealing tamponade of the anastomosed portion of the intestine and continuously compensating for mass movements of the abdomen and in particular peristaltic contractions of the intestine, is maintained in the tamponading balloon body (5, 5b, 5c), so that the tamponading sealing contact of the balloon body (5) with respect to the intestinal wall is continually maintained.

57. The method according to claim 54, characterized in that after the device (1) is inserted in the proper transanal position by the surgeon, the balloon body (5, 5a, 5b, 5c) having tamponading-draining action is connected via a filling line (8) to an extracorporeal reservoir (14) in order to keep the balloon volume and/or the balloon filling pressure constant.

58. The device (1) according to claim 57, characterized in that the extracorporeal reservoir (14) has a balloon that is volume-expandable in a specific manner and made of a material that allows an essentially isobaric pressure profile in the balloon body (5, 5a, 5b, 5c) over a certain expansion range of a wall of the balloon body (5, 5a, 5b, 5c).

59. The device (1) according to claim 57, characterized in that the filling medium is displaceable in both directions between the balloon body (5, 5a, 5b, 5c) and an extracorporeal reservoir (14), without exceeding a maximum pressure in the overall system that is determined by the extracorporeal reservoir (14) via mechanical expansion.

60. The device (1) according to claim 57, characterized in that the reservoir (14) is used as a controlling component in the subsequent post-operative care phase, in which a suture area of the anastomosis (AS) has already stabilized, and particularly precise and rapid control is no longer the primary requirement.

* * * * *